United States Patent [19]

Chang

[11] Patent Number: 4,734,531

[45] Date of Patent: Mar. 29, 1988

[54] SYNTHESIS OF (1-PHENYLETHYL) HYDROQUINONE

[75] Inventor: Shien-Liang Chang, Westlake, Ohio

[73] Assignee: Montedison S.p.A., Milan, Italy

[21] Appl. No.: 50,118

[22] Filed: May 15, 1987

[51] Int. Cl.$^4$ .............................................. C07C 39/14
[52] U.S. Cl. ...................................... 568/744; 568/763
[58] Field of Search .............................. 568/763, 744

[56] References Cited

U.S. PATENT DOCUMENTS

| | | | |
|---|---|---|---|
| 2,247,404 | 7/1941 | Perkins et al. | 568/744 |
| 2,432,356 | 12/1947 | Underwood | 568/744 |
| 2,506,410 | 5/1955 | Blake | 568/744 |
| 2,714,120 | 7/1955 | Kehe | 568/744 |
| 3,772,393 | 11/1973 | Hunter | 568/744 |
| 4,447,593 | 5/1984 | Funakoshi et al. | 528/176 |
| 4,600,765 | 7/1986 | Lee | 528/193 |
| 4,661,645 | 4/1987 | Lee | 568/744 |

FOREIGN PATENT DOCUMENTS 03712  8/1985  World Int. Prop. O. .......... 528/176

OTHER PUBLICATIONS

Kokkyo, "Chemical Abstracts", vol. 101 (1984), 101:210729z.

Kokkyo, "Chemical Abstracts", vol. 101 (1984), 101:210730t.

Yusupov, "Chemical Abstracts", vol. 88 (1978), 88:89256a.

Primary Examiner—Werren B. Lone
Attorney, Agent, or Firm—Robert F. Rywalski

[57] ABSTRACT

An improved process is provided for synthesizing monosubstituted (1-phenylethyl) hydroquinone in high yields and with little contamination by disubstituted (1-phenylethyl) hydroquinone. The process is performed by reacting styrene and hydroquinone using a zeolite molecular sieve.

11 Claims, No Drawings

SYNTHESIS OF (1-PHENYLETHYL) HYDROQUINONE

TECHNICAL FIELD

The present invention relates to substituted hydroquinone compounds and more particularly it relates to the synthesis of (1-phenylethyl) hydroquinone. Even yet more particularly it relates to the synthesis of (1-phenylethyl) hydroquinone to form high yields of the monosubstituted material and virtually no production of any di or higher substituted phenylhydroquinones.

BACKGROUND OF THE INVENTION

U.S. Pat. No. 4,600,765, PCT application publication No. WO85/03712 and co-pending U.S. application Ser. No. 836,902, filed Mar. 6, 1986, all of which are hereby incorporated by reference, disclose a process for forming (1-phenylethyl) hydroquinone by reacting styrene and hydroquinone in the presence of effective catalytic amounts of a Lewis Acid and in the presence of an organic diluent. Unfortunately, as will be readily apparent from those applications and the patent, the process does not provide for a high yield of the monosubstituted (1-phenylethyl) hydroquinone in as much as there are significant amounts of di substituted (including higher degrees of substitution) phenylethyl hydroquinones formed.

Thus it will be appreciated that there is a need in the art to provide for an improved process whereby the yield of (1-phenylethyl) hydroquinone can be increased and the amount of di substituted phenylethyl hydroquinones minimized and effectively virtually eliminated.

DISCLOSURE OF THE INVENTION

In accordance with the present invention, the above need is satisfied. That is in accordance with the present invention a process is provided whereby the yields of (1-phenylethyl) hydroquinone are increased and the formation of di substituted phenylethyl hydroquinones virtually eliminated.

In accordance with this invention, it has been unexpectedly found that zeolite molecular sieves selectively function to increase the yield of (1-phenylethyl) hydroquinone and decrease the output, or formation, of di substituted phenylethyl hydroquinones.

Thus in accordance with this invention, a process is provided for forming (1 phenylethyl) hydroquinone which comprises reacting styrene and hydroquinone in the presence of a zeolite molecular sieve. The zeolites which will be found desirable for the present invention are the type Y molecular sieves which are ion exchanged with ammonium ions. These zeolites are also preferably thermally treated to improve acidic activity. Such type zeolites are well known and widely commercially available. Most desirably the zeolite employed will have a effective pore size of less than about 10 angstroms and preferably a pore size in the range of about 8 to 10 angstroms. For most convenient operation the zeolite molecular sieve will be in a pellet form, commonly produced by chopping extrusions of a zeolite which is bonded with an acid washed inorganic oxide. Two zeolites that have been found to be of outstanding applicability are commercially available from Union Carbide under the commercial designation Linde Molecular Sieves LZ-Y62 1/16" and LZ-Y82 1/16". Of course, other zeolites, especially those having properties closely bordering the properties of these two zeolites or having properties generally intermediate these two zeolites will likewise produce outstanding results.

LZ-Y62 1/16" Molecular Sieves have a unit cell size of about 24.60 angstroms and a surface area of about 670 square meters per gram. Chemically the material contains about 57.1% by weight silica, about 39.8% by weight $Al_2O_3$, about 2.3% by weight of $Na_2O$, about 0.18% by weight CaO and about 0.22% by weight $Fe_2O_3$. The LZ-Y62 1/16" is made of Union Carbide's LZ-Y62 powder bonded with approximately 20% by weight of an acid washed inorganic oxide. LZ-Y62 powder is an ammonium exchanged powder form of a Type Y Molecular Sieve having a low sodium level. Further details of these two molecular sieves can be found in the Union Carbide product sheets also respectively bearing the designations F-3841C 1M 7/79 89-0718 and F-3840D 1M 8/82.

LZ-Y82 1/16" has a surface area (1 PT. B.E.T.) of about 625 square meters per gram and a unit cell size of about 24.45 angstrom units. Chemically the material contains about 65.6% by weight silica, about 33.6% by weight $Al_2O_3$, about 0.15% by weight $Na_2O$, about 0.18 weight percent $Fe_2O_3$ and about 0.03 weight percent of CaO. LZ-Y82 1/16– is made of LZ-Y82 powder bonded with 20% of an acid washed inorganic oxide. These materials contain less than about 0.2 weight percent of alkali metals. LZ-Y82 powder is an ammonium exchanged form of a Type Y Molecular Sieve (LZ-Y72). These materials are described in the Union Carbide product sheets also bearing the designations F-4061B 1M 7/79 89-0723 and F-3843C 1M 7/79 89-0720 and F-3842C 1M 7/79 89-0719.

The present invention is generally practiced in accordance with the processes taught in the above applications and patent but, of course, the reaction is conducted in the presence of the zeolite molecular sieve and subsequent to the reaction the sieves are separated in any convenient manner such as filtration techniques.

As indicated, the reaction is generally conducted in the presence of a diluent. Additionally the separation/purification is preferably done by a vacuum distillation in which a diluent is employed which co-distills with any unreacted hydroquinone under the conditions of vacuum distillation. Preferably the same diluent will be employed during the reaction and the distillation and it will preferably be a liquid polyether like the dialkoxy tetraglycols wherein the alkoxy group contains up to four carbon atoms. In the preferred technique the diluent employed during the reaction and during distillation will be tetraethyleneglycol dimethylether, that is a material of the formula $CH_3(OCH_2CH_2)_4OCH_3$ also known as dimethoxy tetraglycol which is commercially available under the trade designation Tetraglyme material.

In addition to providing a process wherein substantially only monosubstituted (1-phenylethyl) hydroquinone is formed and virtually no di substituted (1-phenylethyl) hydroquinone is formed, the present invention provides for a more economical process than those previously noted. In the past the alkylation of hydroquinone with styrene had a severe limitation; that is, the monosubstituted hydroquinone reacted further with styrene to form di (or higher) alkylated products. The only practical way at that time to help control the additional reactions was to employ excess hydroquinone. This was not cost-effective since hydroquinone is much more expensive than styrene. Additionally, unreacted hydroquinone could not be effectively removed from the reaction mixture without using a diluent which co-distilled with the hydroquinone. These diluents, for example, Tetraglyme material are also quite expensive. Thus in accordance with the present invention excess amounts of hydroquinone will no longer be required and lower amounts of the diluent can be employed during distillation, for example, the Tetraglyme type materials. Hence the process provides for a much more economical production of monosubstituted (1-phenylethyl hydroquinone).

In addition, because little disubstituted material is formed it will be possible in many instances to conduct the distillation at lower temperatures and higher absolute pressure (but still under vacuum) than when large quantities of disubstituted materials are formed. That is, in these instances the desired (1-phenylethyl) hydroquinone can be recovered as the bottom product because there is very little, if any, disubstituted material present. Such processing, of course, provides for economic benefits because of the use of less energy.

In general the process will be practiced by charging the hydroquinone to a reactor and adding a diluent thereto, for example, Tetraglyme material. A stirrer/agitator will be employed, a reflux condenser, suitable heating means and suitable means for charging the styrene. At this point the zeolite can be added to the reactor or it can be added earlier if convenient. Preferably, as indicated above, the zeolites will be in pellet form and the reaction will be desirably conducted by one of two techniques. First of all, the pellets of the zeolite can be positioned on the floor of the reactor and agitation of the reactor will be conducted with the agitator blades disposed above the upper level of the zeolite and the rotational speed being such as not to significantly disrupt or disperse the pellets. In an alternate embodiment, which may generally be employed to decrease the reaction time, the zeolite pellets will be enclosed in a suitable foraminous basket, such as, for example, a basket of stainless steel screening, and the basket attached to the rotating shaft of the agitator; in this way the basket of zeolite pellets is rotated with the rotating agitator shaft and provides intimate contact with the reacting medium.

With the selective zeolite catalyst in position, the reactor is then heated and styrene is added to the system. During the addition of styrene there is a slight exothermic reaction and the temperature is preferably maintained at about 140° C. or so. After the styrene addition is finished the reaction is continued to substantial completion. The product can then be purified and separated in any convenient manner, but preferably high vacuum batch distillation will be employed.

While the above adequately enables one skilled in the art to make and use the present invention, nonetheless further exemplification of the present invention follows.

EXAMPLE AND INDUSTRIAL EXPLOITATION

In the following examples when zeolite is employed the zeolite was positioned on the floor of the reactor, followed by the addition of hydroquinone (HQ) and Tetraglyme material. Styrene was then added and the reaction conducted at the temperature indicated for the time indicated. After that time the reaction products were dissolved in acetone and analyzed, using gas chromatography (Varian OV-17, 6 feet Column, 60° C. to 260° C. at 20° C. per minute and hold at 60° C. for one minute), to determine the amount of monosubstituted (1-phenylethyl) hydroquinone (abbreviated SHQ hereinafter) and the amount of di-substituted phenylethyl hydroquinone (hereinafter abbreviated DSHQ). From this the selectivity, i.e., the ratio of monosubstituted material to disubstituted material was also determined. Table A below summarizes the results of three experiments.

TABLE A

|  | I | II | III |
|---|---|---|---|
| HQ | 119.66 g | 85.5 g | 85.5 g |
| Styrene | 90.34 g | 64.5 g | 64.5 g |
| Tetraglyme Material | 140 g | 100 g | 100 g |
| Catalyst | (0.21 wt %) pTSA | 23.8 g LZ-Y62 (1/16) | 20.5 g LZ-Y62 (1/16) |
| Reaction Temp. (C) | 144 | 140 | 140 |
| Reaction Time (Hrs) | 16.6 | 18.6 | 52.6 |
| SHQ Yield per batch | 26.4 wt % | 32.5 wt % | 31.8 wt % |
| DSHQ Yield (wt %) | 24.5 | 3.51 | 0 |
| Selectivity | 1.08 | 9.26 | Infinity |

In the above pTSA refers to para toluene sulfonic acid. Additionally, in comparing examples II and III it should be pointed out that in Exampe II the stirrer was operated such that some of the LZ-Y62 zeolite was dispersed into the reaction medium and probably encountered a breakdown in its physical structure due to the agitation. This degration of the pellets is believed to have contributed to the higher level of DSHQ. In contrast Example III was run with the blades of the agitator being disposed above the level of zeolite and the agitation being at such a rate that none of the catalyst was dispersed, that is the zeolite remained intact and on the bottom of the reactor. While the reaction time was substantially increased, it will be observed that virtually no DSHQ was formed in Example III.

As generally alluded to above, however, the reaction time can be significantly decreased by enclosing the zeolite pellets in foraminous cage or basket of, for example, stainless steel and attaching it to the rotating agitator shaft. In this way the filled cage or basket acts as an agitator and provides for more intimate reaction mass - zeolite contact. In this way high yields can be maintained and a selectivity of well beyond nine easily achieved.

In passing it may be worthwhile to mention that typically on a commercial scale when practicing the prior art technique of forming the (1-phenylethyl) hydroquinone the SHQ yield was on the order of about 20 to 21%, the DSHA yield on the order of about 10% with a selectivity of about 2.03. Obviously the present invention provides a completely unexpected, improved and superior process having nearly 50% yield increases and allowing for a more lower Tetraglyme usage.

While the invention has been described above with sufficient particularity, it will, of course, be apparent that modifications are possible which pursuant to the patent statutes and laws do not depart from the spirit and scope thereof.

I Claim:

1. In a process for forming (1-phenylethyl) hydroquinone comprising reacting styrene and hydroquinone, the improvement comprising conducting the reaction in the presence of a zeolite molecular sieve.

2. The improvement of claim 1 wherein said zeolite molecular sieve is an ammonium exchanged acidic zeolite.

3. The method of claim 2 wherein said zeolite is in pellet form.

4. The method of claim 3 wherein said zeolite is an ammonium exchanged acidic zeolite bonded with an acid washed inorganic oxide.

5. The method of claim 4 wherein said zeolite is a unit cell size of about 24.60 angstroms in a surface area of about 670 square meters per gram.

6. The method of claim 5 wherein said zeolite contains about 57.1% of $SiO_2$, about 39.8% $Al_2O_3$, about 2.3 weight percent $Na_2O$, about 0.18 weight percent CaO and about 0.22 weight percent $Fe_2O_3$.

7. The method of claim 4 wherein said zeolite as a unit cell size of about 24.45 angstroms and a surface area of about 625 square meters per gram.

8. The method of claim 7 wherein said zeolite contains about 65.6% by weight $SiO_2$, about 33.6% by weight $Al_2O_3$, about 0.15 weight percent of $Na_2O$, about 0.18 weight percent of Fe and about 0.03 weight percent of CaO.

9. The method of claim 1 wherein said zeolite has a pore size of less than 10 angstrom units.

10. The method of claim 9 wherein said zeolite has a pore size of about 8 to about 10 angstrom units.

11. In a method of forming (1-phenylethyl) hydroquinone comprising reacting styrene and hydroquinone to form a reaction product containing monosubstituted (1-phenylethyl) hydroquinone, the improvement comprising conducting the reaction in the presence of a zeolite molecular sieve so as to form substantially all monosubstituted (1-phenylethyl) hydroquinone, said zeolite being a pellet of an ammonium exchanged crystalline sodium aluminosilicate having a low level of sodium and being bonded with an acid washed inorganic oxide.

* * * * *

UNITED STATES PATENT AND TRADEMARK OFFICE
CERTIFICATE OF CORRECTION

PATENT NO. : 4,734,531
DATED      : March 29, 1988
INVENTOR(S): Shien-Liang Chang It is certified that error appears in the above-identified patent and that said Letters Patent is hereby corrected as shown below:

Col. 2, line 25, "1/16-" should be --1/16"--.

Col. 4, line 28, "Exampe" should be --Example--.

Col. 4, line 32, "degration" should be --degradation--.

Claim 8, Column 6, line 3, "Fe" should be --$Fe_2O_3$--.

Signed and Sealed this

Second Day of August, 1988

Attest:

DONALD J. QUIGG

Attesting Officer

Commissioner of Patents and Trademarks